United States Patent
Venugopala et al.

(10) Patent No.: US 11,932,656 B1
(45) Date of Patent: Mar. 19, 2024

(54) THIENO[2,3-d]PYRIMIDINES AS COX-2 INHIBITORS

(71) Applicant: KING FAISAL UNIVERSITY, Al-Ahsa (SA)

(72) Inventors: Katharigatta N. Venugopala, Al-Ahsa (SA); Pran Kishore Deb, Ranchi (IN); Raghu Prasad Mailavaram, Maharashtra (IN); Nizar A. Al-Shar'i, Ar-Ramtha (JO); Swastika Ganguly, Ranchi (IN); Bapi Gorain, Ranchi (IN); Lim Tse Mun, Kuala Lumpur (MY); Jamie Kow Kean Hing, Kuala Lumpur (MY)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/377,459

(22) Filed: Oct. 6, 2023

(51) Int. Cl.
*C07D 495/04* (2006.01)
*A61P 29/00* (2006.01)

(52) U.S. Cl.
CPC ............ *C07D 495/04* (2013.01); *A61P 29/00* (2018.01)

(58) Field of Classification Search
CPC ................................ C07D 495/04; A61P 29/00
See application file for complete search history.

(56) References Cited

U.S. PATENT DOCUMENTS

| | | |
|---|---|---|
| 7,378,411 B2 | 5/2008 | Fraley et al. |
| 2013/0102601 A1 | 4/2013 | Classen-Houben et al. |

OTHER PUBLICATIONS

Pubchem, 2-[(4-Fluorophenyl)Methyl]-5,6-Dimethyl-3H-Thieno[2,3-D]Pyrimidin-4-One, Nov. 26, 2010.
Pubchem, 2-[(4-Methoxyphenyl)Methyl]-5,6-Dimethyl-3H-Thieno[2,3-D]Pyrimidin-4-One, May 28, 2009.
Zhang, et al., "Design, Synthesis, and Biological Activity of Tetrahydrobenzo[4,5]Thieno[2,3-D] Pyrimidine Derivatives as Anti-Inflammatory Agents", Molecules, 2017, 22(11), 1960.

*Primary Examiner* — Rebecca L Anderson
(74) *Attorney, Agent, or Firm* — Nath, Goldberg & Meyer; Richard C. Litman

(57) ABSTRACT

Methods of inhibiting cyclooxygenase enzyme-2 (COX-2) using thieno[2,3-d]pyrimidine compounds. These methods can be effective for treating inflammation, pain, or any other COX-2 mediated disorder.

16 Claims, No Drawings

THIENO[2,3-d]PYRIMIDINES AS COX-2 INHIBITORS

BACKGROUND

1. FIELD

The present disclosure provides thieno[2,3-d]pyrimidines used as COX-2 inhibitors, compositions containing such compounds, and methods of their preparation. These compounds and compositions are useful as therapeutic agents for treatment of pathological conditions or diseases that can be improved by COX-2 modulation.

2. DESCRIPTION OF THE RELATED ART

Non-steroidal anti-inflammatory drugs (NSAIDs) have been therapeutically used in the medication of rheumatic arthritis and also in the treatment of various inflammatory disorders. Due to their gastrointestinal side effects, they can at times be used in limited numbers. Further, COX-2 inhibitors have been evaluated for their ability to treat inflammation but have often exhibited similar side effects to certain NSAIDs.

Accordingly, there remains a need for new treatments for inflammation having a decreased incidence of side effects. Thus, the new use of compounds as COX-2 inhibitors solving the aforementioned problems are desired.

SUMMARY

The present subject matter pertains to the field of pharmaceuticals, particularly to certain 2-(substituted benzyl)-5,6-dimethylthieno[2,3-d]pyrimidin-4(3H)-ones and N-(5,6-dimethyl-4-oxo-3,4-dihydrothieno[2,3-d]pyrimidin-2-yl)-substituted benzamides used as cyclooxygenase-2 (COX-2) inhibitors, and as anti-inflammatory agents.

In an effort to develop novel anti-inflammatory agents, a series of 2-(substituted benzyl)-5,6-dimethylthieno[2,3-d]pyrimidin-4(3H)-ones and N-(5,6-dimethyl-4-oxo-3,4-dihydrothieno[2,3-d]pyrimidin-2-yl)-substituted benzamides have been achieved by a synthetic chemical method and purified by recrystallization and column chromatographic methods. Structural elucidation of the compounds has been completed by spectral techniques such as FT-IR, NMR ($^1$H and $^{13}$C), LC-MS, and elemental analysis. The present compounds show promising anti-inflammatory activity between millimolar to micromolar concentrations compared to standard anti-inflammatory drugs. Some of the selected lead compounds can be successfully taken forward to develop novel anti-inflammatory drug candidates.

In an embodiment, the present subject matter relates to a compound used as an anti-inflammatory agent or for inhibiting COX-2 having the formula I:

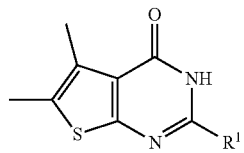

or a pharmaceutically acceptable salt, ester, stereoisomer, or solvate thereof, wherein:

$R_1$ is selected from the group consisting of —$CH_2$-phenyl and —NH-(C=O)-phenyl, wherein the phenyl in either of the —$CH_2$-phenyl and —NH-(C=O)-phenyl is substituted with one substituent selected from the group consisting of a halogen, methoxy, and $CF_3$.

In another embodiment, the present subject matter relates to a compound used as an anti-inflammatory agent or for inhibiting COX-2 having the formula I:

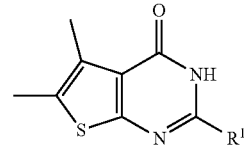

or a pharmaceutically acceptable salt, ester, stereoisomer, or solvate thereof, wherein:

$R_1$ is selected from the group consisting of —$CH_2$-phenyl and —NH-(C=O)-phenyl, wherein the phenyl in either of the —$CH_2$-phenyl and —NH-(C=O)-phenyl is substituted with one substituent selected from the group consisting of fluorine, methoxy, and $CF_3$.

In an embodiment, the present subject matter relates to a compound used as an anti-inflammatory agent or for inhibiting COX-2 selected from the group consisting of: 2-(4-Fluorobenzyl)-5,6-dimethylthieno[2,3-d]pyrimidin-4(3H)-one (4a); 2-(4-Methoxybenzyl)-5,6-dimethylthieno[2,3-d]pyrimidin-4(3H)-one (4b); N-(5,6-Dimethyl-4-oxo-3,4-dihydrothieno[2,3-d]pyrimidin-2-yl)-4-fluorobenzamide (5a); N-(5,6-dimethyl-4-oxo-3,4-dihydrothieno[2,3-d]pyrimidin-2-yl)-2-(trifluoromethyl)benzamide (5b); and a pharmaceutically acceptable salt, ester, stereoisomer, or solvate thereof.

In an embodiment, the present subject matter relates to a process for the synthesis of the compounds of formula I, including a number of species or specific structures falling under structural formula I. Further contemplated herein are pharmaceutical compositions containing these compounds, as well as methods of inhibiting COX-2 and of treating pathological conditions or diseases that can be improved by COX-2 inhibition, such as inflammation, by administering the present compounds to a patient in need thereof.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms, and can be referred to as a "lower alkyl group" or a "$C_1$-$C_6$ alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group) or 2 to 6 carbon atoms (i.e., $C_2$-$C_6$ alkenyl group). In some embodiments, alkenyl groups can be substituted as described herein. An alkenyl group is generally not substituted with another alkenyl group, an alkyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

The term "substituted alkenyl" refers to an alkenyl group in which 1 or more (up to about 5, for example about 3) hydrogen atoms is replaced by a substituent independently selected from those listed above with respect to a substituted alkyl. Other alkenyl substituents as described herein may further be contemplated.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C6F5), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), SiH$_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as disorder that can be treated by COX-2 inhibition, such as inflammation.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter pertains to the field of pharmaceuticals, particularly to certain 2-(substituted benzyl)-5,6-dimethylthieno[2,3-d]pyrimidin-4(3H)-ones and N-(5,6-dimethyl-4-oxo-3,4-dihydrothieno[2,3-d]pyrimidin-2-yl)-substituted benzamides used as COX-2 inhibitors, and as anti-inflammatory agents.

In an effort to develop novel anti-inflammatory agents, a series of 2-(substituted benzyl)-5,6-dimethylthieno[2,3-d]pyrimidin-4(3H)-ones and N-(5,6-dimethyl-4-oxo-3,4-dihydrothieno[2,3-d]pyrimidin-2-yl)-substituted benzamides have been achieved by a synthetic chemical method and purified by recrystallization and column chromatographic methods. Structural elucidation of the compounds has been completed by spectral techniques such as FT-IR, NMR ($^1$H and $^{13}$C), LC-MS, and elemental analysis. The present compounds show promising anti-inflammatory activity between millimolar to micromolar concentrations compared to standard anti-inflammatory drugs. Some of the selected lead compounds can be successfully taken forward to develop novel anti-inflammatory drug candidates.

In an embodiment, the present subject matter relates to a compound used as an anti-inflammatory agent or for inhibiting COX-2 having the formula I:

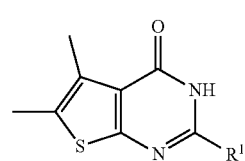

I or a pharmaceutically acceptable salt, ester, stereoisomer, or solvate thereof, wherein:

R₁ is selected from the group consisting of —CH₂-phenyl and —NH-(C═O)-phenyl, wherein the phenyl in either of the —CH₂-phenyl and —NH-(C═O)-phenyl is substituted with one substituent selected from the group consisting of a halogen, methoxy, and CF₃.

In a further embodiment, the present subject matter relates to use of a compound of formula I, wherein R₁ is —CH₂-phenyl. In an embodiment in this regard, the present subject matter relates to use of a compound of formula I, wherein the phenyl in the —CH₂-phenyl has one substituent which is a halogen or a methoxy. In another embodiment in this regard, the present subject matter relates to use of a compound of formula I, wherein the phenyl in the —CH₂-phenyl has one substituent which is a fluorine or a methoxy. In a further embodiment, the substituent can be at the 4-position of the phenyl.

In another embodiment, the present subject matter relates to use of a compound of formula I, wherein R₁ is —NH-(C═O)-phenyl. In an embodiment in this regard, the present subject matter relates to use of a compound of formula I, wherein the phenyl in the —NH-(C═O)-phenyl has one substituent which is a halogen or a CF₃. In yet another embodiment in this regard, the present subject matter relates to use of a compound of formula I, wherein the phenyl in the —NH-(C═O)-phenyl has one substituent which is a fluorine or a CF₃. In certain embodiments, the fluorine can be at the 4-position of the phenyl or the CF₃ can be at the 2-position of the phenyl.

In an embodiment, the present subject matter relates to a compound used as an anti-inflammatory agent or for inhibiting COX-2 having the formula I:

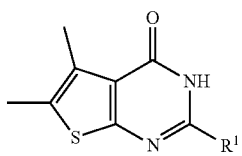

I or a pharmaceutically acceptable salt, ester, stereoisomer, or solvate thereof, wherein:

R₁ is selected from the group consisting of —CH₂-phenyl and —NH-(C═O)-phenyl, wherein the phenyl in either of the -CH2-phenyl and -NH-(C=0)-phenyl is substituted with one substituent selected from the group consisting of fluorine, methoxy, and CF₃.

In an embodiment, the present subject matter relates to a compound used as an anti-inflammatory agent or for inhibiting COX-2 selected from the group consisting of: 2-(4-Fluorobenzyl)-5,6-dimethylthieno[2,3-d]pyrimidin-4(3H)-one (4a); 2-(4-Methoxybenzyl)-5,6-dimethylthieno[2,3-d]pyrimidin-4(3H)-one (4b); N-(5,6-Dimethyl-4-oxo-3,4-dihydrothieno[2,3-d]pyrimidin-2-yl)-4-fluorobenzamide (5a); N-(5,6-dimethyl-4-oxo-3,4-dihydrothieno[2,3-d]pyrimidin-2-yl)-2-(trifluoromethyl)benzamide (5b); and a pharmaceutically acceptable salt, ester, stereoisomer, or solvate thereof.

Said differently, the present subject matter can relate to compounds of formula I selected from the group consisting of:

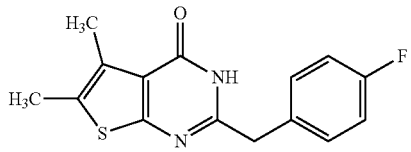

4a

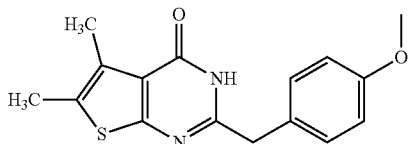

4b

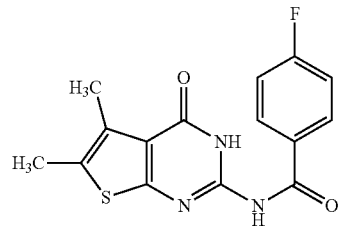

5a

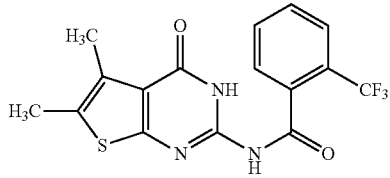

5b and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to one of the following general synthetic pathways. Specifically, synthesis commences with adding 2-butanone, ethanol, ethylcyanoacetate, and sulphur to a flask and heating to about 55° C. to about 65° C. Diethylamine is then added dropwise and the reaction mixture is stirred for at least about 5 hours and cooled to room temperature. The solution is then maintained at a temperature of about 4° C. for at least about 24 hours. Crystals form, which are filtered, dried, and re-crystallized to obtain compound (4).

In one synthetic pathway, compound 4 is used to make 4a or 4b. In this regard, compound 4 and 4-fluorophenyl acetonitrile or 4-methylphenyl acetonitrile in 1,4-dioxane are taken in a flask and a stream of dry hydrochloric acid gas is passed through the mixture for at least about 24 hours. Then, neutralization is carried out with sufficient dilute sodium hydroxide solution (10% NaOH). The resultant precipitate is filtered, dried, and recrystallized from ethanol to yield 4a or 4b.

In another synthetic pathway, compound 4, cyanamide, and concentrated HCl solution are added into a round bottom flask and refluxed for at least about 12 hours at about 45° C. Then, the reaction mixture is neutralized with diluted NaOH (10%) solution. The precipitate formed is filtered, dried and re-crystalized with ethanol to obtain pure product (5).

The compound (5) is then completely dissolved into DMF in a round bottom flask with constant stirring. The mixture is cooled to room temperature and placed into an ice bath (0-5° C.) followed by the addition of NaH. After at least about one hour, 4-fluorobenzoyl chloride or 2-(trifluoromethyl)benzoyl chloride is added dropwise with a syringe and stirred for at least about 24 hours. The reaction mixture is neutralized with diluted NaOH (10%) solution and extracted with ice. The precipitate formed is filtered and dried. The aqueous layer is extracted further with ethyl acetate and evaporated. The crude reaction compound is purified to obtain a pure product 5a or 5b.

The synthetic scheme is seen as outlined in Scheme 1.

Scheme-1

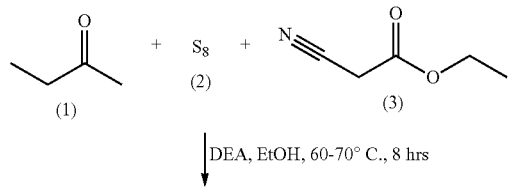

DEA, EtOH, 60-70° C., 8 hrs

-continued

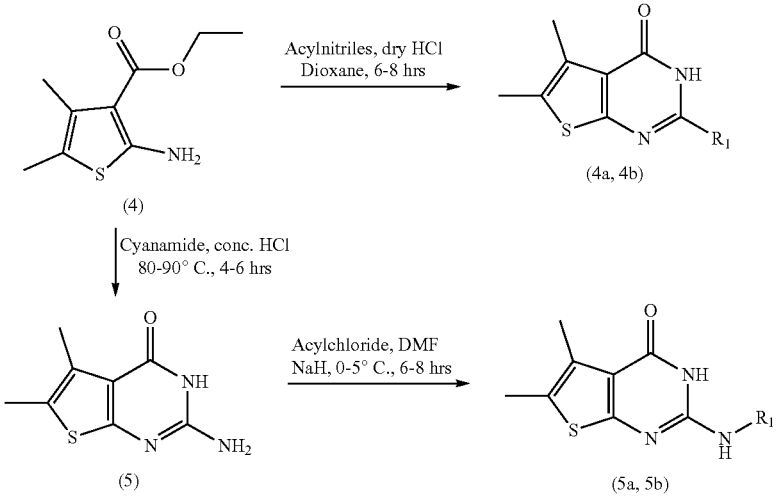

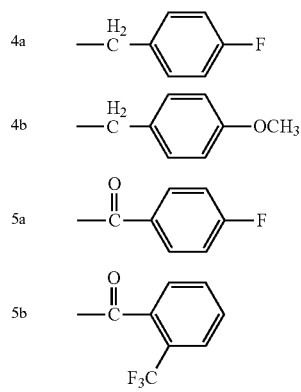

| Compound No. | $R_1$ |
|---|---|
| 4a | —CH$_2$—C$_6$H$_4$—F |
| 4b | —CH$_2$—C$_6$H$_4$—OCH$_3$ |
| 5a | —C(O)—C$_6$H$_4$—F |
| 5b | —C(O)—C$_6$H$_4$(CF$_3$) |

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one or two of the present compounds, or one of the present compounds.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for cancer. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of as a COX-2 inhibitor, such as treating inflammation, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the present compounds for the treatment of pathological conditions or diseases mediated by COX-2 inhibition, such as inflammation, or pain, or any other COX-2 mediated disorder. Similarly, the present compounds can be used to inhibit COX-2 in a patient.

In this regard, the present compounds can exhibit a COX-2 $IC_{50}$ of about 40 to about 190, or about 42, about 142, about 103, or about 189, µM.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used. Similarly, one or more of the present compounds can be used in combination therapy with one or more additional active agents.

The following examples relate to various methods of manufacturing certain specific compounds as described herein. All compound numbers expressed herein are with reference to the synthetic pathway figures shown above.

EXAMPLES

Materials and Methods

2-Butanone, ethylcyanoacetate (≥98%), dimethylformamide (≥99.5%), ethanol (≥99%), n-hexane, cyanamide and sulphur (≥99.5%) were bought from Acros Chemical (USA). Diethylamine, sodium sulphate anhydrous and analytical grade NaOH pellets were bought from Fisher Scientific (UK). 1,4-dioxane, concentrated HCl, ethyl acetate, hexane, chloroform, 4-fluorobenzoyl chloride (98%), 4-methoxyphenyl acetonitrile (≥97%), 4-fluorophenyl acetonitrile (≥99%), and 2-(trifluoromethyl)benzoyl chloride were bought from Aldrich Chemicals. TLC Silica gel 60 F254 was obtained from Merck, USA. COX inhibitor screening assay kit (Item no. 560131) was procured from Cayman Chemical, USA.

Identification, progression, purity and Rf values of the synthesized compounds were determined by using silica gel-coated TLC plate. UV-lamp (Perkin Elmer Lambda 25) at 254 nm was used to visualize the TLC spots present on the plate. Melting points of synthesized compounds were carried out in open glass capillary tubes by using Stuart Melting Point Apparatus SMP11. The infrared spectra of synthesized compounds were determined by Shimadzu 8400S spectrophotometer with wavenumbers ranging from 500-4000 $cm^{-1}$. The proton ($^1H$) NMR spectra were determined by using VARIAN 500 MHz instrument where the chemical shifts were recorded in δ (ppm) downfield from tetramethylsilane (TMS). The splitting patterns were represented as follows: s, singlet; d, doublet; m, multiplet. Mass of the synthesized compounds was confirmed by using Shimadzu GCMS -QP2010 Plus spectrophotometer.

Example 1

Synthesis of Ethyl-2-amino-4,5-dimethylthiophene-3-carboxylate (4)

2-Butanone (0.04 mol, 3.61 ml), ethanol (30 ml), ethylcyanoacetate (0.04 mol, 4.52 ml) and sulphur (0.04 mol, 1.28 g) was added into a conical flask and heated at 60° C. Diethylamine (0.04 mol, ml) was then added dropwise, stirred for five hours and cooled to room temperature. The solution was kept into the fridge at 4° C. for 24 hours. The crystals formed were filtered, dried and re-crystalized with ethanol to obtain compound (4).

Yield: 60%. Orange yellow crystals, mp. 89-91, Rf ($CHCl_3$: Acetone, 9:1)=0.89, FT-IR (KBR, $cm^{-1}$): 3398.57, 3294.42 ($NH_2$); 2980.02, 2926.01 (aliphatic C—H); 1643.35 (C=O); 1593.20 (C=C); 1573.91 (N—H bend); 1479.40 ($CH_2$ bend); 1375.25 ($CH_3$ bend); 1262.32 (C—N). $^1H$ NMR ($CDCl_3$) δ ppm: 4.288-4.246 (m, 2H, 3-$CH_2$); 2.159 (s, 3H, 5-$CH_3$); 2.135 (s, 3H, 4-$CH_3$); 1.353-1.325 (t, 3H, 3-$CH_3$). ESI-MS (m/z; %)=199.07 ($M^+$+1; 100).

Example 2

Synthesis of 2-amino-5,6-dimethylthieno[2,3-d]pyrimidin-4(3H)-one (5)

The compound (4) (0.01 mol, 2 g), cyanamide (2 g) and concentrated HCl solution (2 ml) was added into a round bottom flask and refluxed for 12 hours at 45° C. Then, the reaction mixture was neutralized with diluted NaOH (10%) solution. The precipitate formed was filtered, dried and re-crystalized with ethanol to obtain pure product (5).

Yield: 90%. White powder, mp. >300, Rf ($CHCl_3$: Acetone, 9:1)=0.05, FT-IR (KBR, $cm^{-1}$): 3408.22 ($NH_2$); 3309.85 (N—H stretch); 2902.87 (aliphatic C—H); 1654.92 (C=O); 1614.42 (N—H bend); 1591.27 (C=C); 1263.52 (C—N). $^1H$ NMR ($CDCl_3$) δ ppm: 10.736 (s, 1H, 3-NH); 6.380 (s, 2H, 2-$NH_2$); 2.462 (s, 3H, 6-$CH_3$); 2.188 (s, 3H, 5-$CH_3$). ESI-MS (m/z; %)=195.05 ($M^+$+1; 100).

Example 3

Synthesis of 2-(4-Fluorobenzyl)-5,6-dimethylthieno [2,3-d]pyrimidin-4(3H)-one (4a)

Compound 4 (0.02 mol; 2.00 g) and 4-fluorophenyl acetonitrile (0.03 mol; 1.80 ml) in 1,4-dioxane (0.02 mol; 8.00 ml) were taken in conical flask and a stream of dry hydrochloric acid gas was passed through the mixture for 24 hours. Then, neutralization was carried out with sufficient dilute sodium hydroxide solution (10% NaOH). The resultant precipitate was filtered, dried and recrystallized from ethanol to yield the compound 4a.

Yield: 88.68%. White powder, mp. 291, Rf (Hexane: EtAc, 6:4)=0.53, FT-IR (KBR, $cm^{-1}$): 3304 (2° Amides N—H), 3068 (Aromatic =C—H), 3005 (Alkanes C—H), 2920 (Alkanes C—H), 1645 (Amides C=O), 1600 (Aromatic C=C), 1504 (2° Amines N—H), 1471 (Aromatic C=C), 1207 (Amines C—N), 1381 (Alkanes $CH_3$), 1029 (Fluorides C—F), 858 (para-disubstituted rings). $^1H$ NMR ($CDCl_3$) δ ppm: 4.288-4.246 (q, 2H, 3-$COOCH_2$), 2.159 (s, 3H, 5-$CH_3$), 2.135 (s, 3H, 4-$CH_3$), 1.353-1.325 (t, 3H, 3-$COOCH_2CH_3$), ESI-MS (m/z; %)=288.0 ($M^+$+1; 100).

Example 4

Synthesis of 2-(4-Methoxybenzyl)-5,6-dimethylthieno[2,3-d]pyrimidin-4(3H)-one (4b)

Compound 4 (0.02 mol; 2.00 g) and 4-methoxyphenyl acetonitrile (0.03 mol; 2.00 ml) in 1,4-dioxane (0.02 mol; 8.00 ml) were taken in conical flask and a stream of dry hydrochloric acid gas was passed through the mixture for 24 hours. Then, neutralization was carried out with sufficient dilute sodium hydroxide solution (10% NaOH). The resultant precipitate was filtered, dried and recrystallized from ethanol to yield the compound 4b.

Yield: 85.37%. White powder, mp. >300, Rf (Hexane: EtAc, 6:4)=0.55, FT-IR (KBR, cm$^{-1}$): 3304 (2° Amides N—H), 3005 (Alkanes C—H), 3095 (Aromatic =C—H), 1581 (2° Amines N—H Bending), 1651 (Amides C=O), 1608 (Aromatic C=C), 1508 (Alkanes $CH_2$), 1475 (Aromatic C=C), 1381 (Alkanes $CH_3$), 1298 (Amines C—N), 1242 (Ethers C—O), 817 (para-disubstituted rings). $^1$H NMR (CDCl$_3$) δ ppm: 4.288-4.246 (q, 2H, 3-COOCH$_2$), 2.159 (s, 3H, 5-CH$_3$), 2.135 (s, 3H, 4-CH$_3$), 1.353-1.325 (t, 3H, 3-COOCH$_2$CH$_3$). 12.363 (s, 1H, 3-NH), 7.240-6.844 (m, 4H, 2-CH$_2$C$_6$H$_4$), 3.804 (s, 2H, 2-CH$_2$), 3.689-3.554 (s, 3H, 2-CH$_2$C$_6$H$_4$OCH$_3$), 2.480 (s, 3H, 6-CH$_3$), 2.329-2.292 (s, 3H, 5-CH$_3$). ESI-MS (m/z; %)=300.0 (M$^+$+1; 100).

Example 5

Synthesis of 2-(4-fluorobenzamido)-5,6-dimethylthieno[2,3-d]pyrimidin-4(3H)-one (5a)

The compound (5) (0.002 mol, 0.390 g) was completely dissolved into DMF (5ml) in a round bottom flask with constant stirring. The mixture was cooled to room temperature and placed into an ice bath (0-5° C.) followed by the addition of NaH (0.008 mol, 0.192 g). After an hour, 4-fluorobenzoyl chloride (0.003 mol, 0.35 ml) was added dropwise with a syringe and stirred for 24 hours. The reaction mixture was neutralized with diluted NaOH (10%) solution and extracted with ice. The precipitate formed was filtered and dried. The aqueous layer was extracted further with ethyl acetate and evaporated. The crude reaction compound was purified using column chromatography (Hexane: Ethylacetate:9.2:0.8) to obtain a pure product (5a).

Yield: 30%. White powder, mp. >300, Rf (CHCl$_3$: Acetone, 9:1)=0.85, FT-IR (KBR, cm$^{-1}$): 3317.56, 3230.77 (N—H stretch), 3120.82 (aromatic C—H); 2912.51, 2848.86 (aliphatic C—H); 1674.21 (C=O); 1651.07 (aromatic C=C); 1589.34 (N—H bend); 1381.03 (C—H); 1309.67 (C—N); 1249.38 (C—F); 849.78 (para-substituted ring). $^1$H NMR (CDCl$_3$) δ ppm: 12.101 (s, 1H, 2NH); 11.887 (s, 1H, 3NH); 8.118-7.353 (m, 4H, 2C$_6$H$_4$); 2.518 (s, 3H, 6CH$_3$); 2.354 (s, 3H, 5CH$_3$). ESI-MS (m/z; %)=317.06 (M$^+$+1; 100).

Example 6

Synthesis of 2-(trifluromethylbenzamido)-5,6-dimethylthieno[2,3-d]pyrimidin-4(3H)-one (5b)

The compound (5) (0.002 mol, 0.390 g) was completely dissolved into DMF (5 ml) in a round bottom flask with constant stirring. The mixture was cooled to room temperature and placed into an ice bath (0-5° C.) followed by the addition of NaH (0.008 mol, 0.192 g). After an hour, 2-(trifluoromethyl)benzoyl chloride (0.003 mol, 0.44 ml) was added dropwise with a syringe and stirred for 24 hours. The reaction mixture was neutralized with diluted NaOH (10%) solution and extracted with ice. The precipitate formed was filtered and dried. The aqueous layer was extracted further with ethyl acetate and evaporated. The crude reaction compound was purified using column chromatography (Hexane:Ethylacetate:9.2:0.8) to obtain a pure product (5b).

Yield: 25%. White powder, mp. >300, Rf (CHCl$_3$: Acetone, 9:1)=0.85, FT-IR (KBR, cm$^{-1}$): 3224.98 (N—H stretch); 3186.40 (C—H sp$^2$ stretch); 2954.95, 2916.37, 2848.86 (aliphatic C—H); 1654.92 (C=O); 1597.06 (aromatic C=C); 1556.55 (N—H bend); 1369.46 (C—N); 1311.59 (C—F); 1261.45 (in plane C—H bend); 756.10 (ortho-disubstituted ring). $^1$H NMR (CDCl$_3$) δ ppm: 12.142 (s, 1H, 2-NH); 11.877 (s, 1H, 3-NH); 7.864-7.688 (m, 4H, 2-C$_6$H$_4$); 2.365 (s, 3H, 6-CH$_3$); 2.321 (s, 3H, 5-CH$_3$). ESI-MS (m/z; %)=367.06 (M$^+$+1; 100).

Pharmacological Activity

Example 7

In vitro Cyclooxygenase Inhibition Activity

The COX (ovine) Inhibitor Screening Assay was performed mainly to determine the selective inhibition of tested compounds (4a, 4b, 5a, 5b) towards the ovine COX-1 and human recombinant COX-2 isoenzymes. The addition of arachidonic acid (AA) helped to convert the COX component into PGG$_2$, followed by reduction of PGG$_2$ into PGH$_2$. The following addition of SnCl$_2$ converted PGH$_2$ into PGF$_{2\alpha}$. The assay directly measures the PGF$_2$0 via enzyme immunoassay (EIA) using a broadly specific antiserum that bound to all PG tracers. Depending on the tested compounds inhibitory effect, the concentration of PGF$_{2\alpha}$ in each well varied and was inversely proportional to the amount of PG tracers that was able to bind to the antiserum. PG tracers-antiserum complex was left to bind to the mouse monoclonal anti-rabbit antibody that has been coated to the well during the 18 hours incubation. Ellman's reagent was added to give distinct yellow coloration to the products from this enzymatic reaction, which absorbed strongly at 412 nm. The intensity of the color was proportional to the amount of PG tracers-antiserum complex bound to the well, which was inversely proportional to the concentration of PGF$_{2\alpha}$ present.

The inhibitory activity of tested compounds was determined based on IC$_{50}$ values whereas the selectivity was based on their selectivity indices (SI), which defined as COX-1 IC$_{50}$/COX-2 IC$_{50}$. In the assay system, indomethacin was used as non-selective COX inhibitor standard while NS-398 was used as COX-2 selective inhibitor standard. The results revealed that both tested compounds (4a, 4b, 5a, 5b)) were showing mild selective inhibition against COX-2 as listed in Table 1.

TABLE 1

Anti-inflammatory results of 2-(substituted benzyl)-5,6-dimethylthieno[2,3-d]pyrimidin-4(3H)-ones (4a and 4b) and N-(5,6-dimethyl-4-oxo-3,4-dihydrothieno[2,3-d]pyrimidin-2-yl)-substituted benzamides (5a and 5b) in μg/mL.

| Compound code | Compound Structure | Anti-inflammatory activity | | |
|---|---|---|---|---|
| | | COX-1 IC$_{50}$ (μM) | COX-2 IC$_{50}$ (μM) | SI |
| 4a | 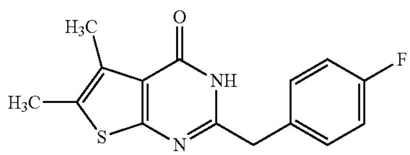 [SMILES: Cc1sc2nc(Cc3ccc(F)cc3)[nH]c(=O)c2c1C] | 202.96 | 42.19 | 4.81 |
| 4b | 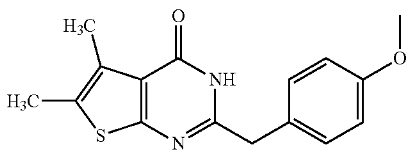 | 586.07 | 142.71 | 4.11 |
| 5a | 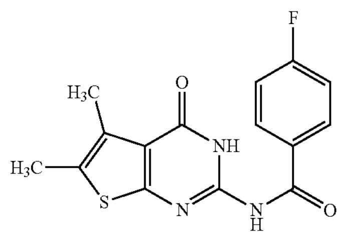 [SMILES: Cc1sc2nc(NC(=O)c3ccc(F)cc3)[nH]c(=O)c2c1C] | 111.79 | 103.47 | 1.08 |
| 5b | 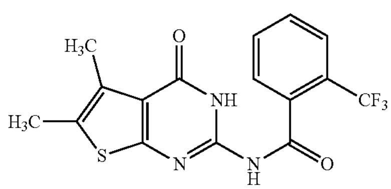 [SMILES: Cc1sc2nc(NC(=O)c3ccccc3C(F)(F)F)[nH]c(=O)c2c1C] | 21.84 | 189.05 | 0.12 |

It is to be understood that the use of the thieno[2,3-d] pyrimidines compounds are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of inhibiting cyclooxygenase-2 (COX-2) in a patient comprising administering to a patient in need thereof a compound having the formula I:

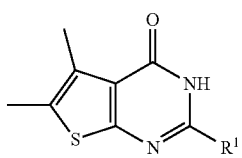

I or a pharmaceutically acceptable salt, ester, stereoisomer, or solvate thereof, wherein:

$R_1$ is selected from the group consisting of —CH$_2$-phenyl and —NH-(C=O)-phenyl,
wherein the phenyl in either of the —CH$_2$-phenyl and —NH-(C=O)-phenyl is substituted with one substituent selected from the group consisting of a halogen, methoxy, and CF$_3$.

2. The method of claim 1, wherein $R_1$ is —CH$_2$ phenyl.

3. The method of claim 2, wherein the phenyl in the —CH$_2$-phenyl has one substituent which is a halogen or a methoxy.

4. The method of claim 2, wherein the phenyl in the —CH$_2$-phenyl has one substituent which is a fluorine or a methoxy.

5. The method of claim 2, wherein the substituent is at the 4-position of the phenyl.

6. The method of claim 1, wherein $R_1$ is —NH-(C=O)-phenyl.

7. The method of claim 6, wherein the phenyl in the —NH-(C=O)-phenyl has one substituent which is a halogen or a CF$_3$.

8. The method of claim 6, wherein the phenyl in the —NH-(C=O)-phenyl has one substituent which is a fluorine or a CF$_3$.

9. The method of claim 1, wherein the inhibition of COX-2 is effective for treating inflammation in the patient.

10. The method of claim 1, wherein the inhibition of COX-2 is effective for treating pain in the patient.

11. A method of inhibiting cyclooxygenase-2 (COX-2) in a patient comprising administering to a patient in need thereof a compound having the formula I:

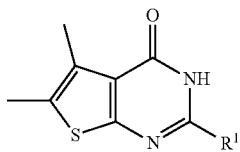

or a pharmaceutically acceptable salt, ester, stereoisomer, or solvate thereof, wherein:
$R_1$ is selected from the group consisting of —CH$_2$-phenyl and —NH-(C=O)-phenyl,
wherein the phenyl in either of the —CH$_2$-phenyl and —NH-(C=O)-phenyl is substituted with one substituent selected from the group consisting of fluorine, methoxy, and CF$_3$.

12. The method of claim 11, wherein the inhibition of COX-2 is effective for treating inflammation in the patient.

13. The method of claim 11, wherein the inhibition of COX-2 is effective for treating pain in the patient.

14. A method of inhibiting cyclooxygenase-2 (COX-2) in a patient comprising administering to a patient in need thereof a compound selected from the group consisting of:
2-(4-Fluorobenzyl)-5,6-dimethylthieno[2,3-d]pyrimidin-4(3H)-one (4a);
2-(4-Methoxybenzyl)-5,6-dimethylthieno[2,3-d]pyrimidin-4(3H)-one (4b);
N-(5,6-Dimethyl-4-oxo-3,4-dihydrothieno[2,3-d]pyrimidin-2-yl)-4-fluorobenzamide (5a);
N-(5,6-dimethyl-4-oxo-3,4-dihydrothieno[2,3-d]pyrimidin-2-yl)-2-(trifluoromethyl)benzamide (5b);
and a pharmaceutically acceptable salt, ester, stereoisomer, or solvate thereof.

15. The method of claim 14, wherein the inhibition of COX-2 is effective for treating inflammation in the patient.

16. The method of claim 14, wherein the inhibition of COX-2 is effective for treating pain in the patient.

* * * * *